United States Patent
Yamamori et al.

(10) Patent No.: US 9,370,340 B2
(45) Date of Patent: Jun. 21, 2016

(54) ULTRASONIC DIAGNOSTIC APPARATUS AND ULTRASONIC DIAGNOSIS ASSISTING METHOD

(71) Applicants: Kabushiki Kaisha Toshiba, Tokyo (JP); Toshiba Medical Systems Corporation, Otawara-shi (JP)

(72) Inventors: Kyohei Yamamori, Otawara (JP); Tomohiro Kawasaki, Otawara (JP); Kensuke Shinoda, Otawara (JP)

(73) Assignees: KABUSHIKI KAISHA TOSHIBA, Tokyo (JP); TOSHIBA MEDICAL SYSTEMS CORPORATION, Otawara-shi (JP)

( * ) Notice: Subject to any disclaimer, the term of this patent is extended or adjusted under 35 U.S.C. 154(b) by 109 days.

(21) Appl. No.: 13/785,328

(22) Filed: Mar. 5, 2013

(65) Prior Publication Data

US 2013/0237827 A1    Sep. 12, 2013

(30) Foreign Application Priority Data

Mar. 7, 2012   (JP) ................................ 2012-050926

(51) Int. Cl.
| | |
|---|---|
| A61B 5/02 | (2006.01) |
| A61B 6/00 | (2006.01) |
| A61B 8/08 | (2006.01) |
| A61B 8/00 | (2006.01) |
| A61B 8/12 | (2006.01) |
| A61B 8/13 | (2006.01) |

(52) U.S. Cl.
CPC .............. *A61B 8/5207* (2013.01); *A61B 8/0883* (2013.01); *A61B 8/0891* (2013.01); *A61B 8/12* (2013.01); *A61B 8/4245* (2013.01); *A61B 8/4254* (2013.01); *A61B 8/461* (2013.01); *A61B 8/463* (2013.01); *A61B 8/54* (2013.01); *A61B 8/13* (2013.01)

(58) Field of Classification Search
CPC ...... A61B 8/0883; A61B 8/0891; A61B 8/12; A61B 8/13; A61B 8/4245
USPC .................................. 600/423, 424, 443, 454
See application file for complete search history.

(56) References Cited

U.S. PATENT DOCUMENTS

| | | | | |
|---|---|---|---|---|
| 2002/0169496 | A1* | 11/2002 | Wallace et al. | .............. 623/1.13 |
| 2005/0038343 | A1* | 2/2005 | Cao et al. | ...................... 600/454 |

(Continued)

FOREIGN PATENT DOCUMENTS

| | | |
|---|---|---|
| JP | 2006-263241 | 10/2006 |
| JP | 2010-119850 | 6/2010 |

*Primary Examiner* — Baisakhi Roy
(74) *Attorney, Agent, or Firm* — Oblon, McClelland, Maier & Neustadt, L.L.P.

(57) ABSTRACT

An ultrasonic diagnostic apparatus includes an image generating unit, an acquiring unit, an extracting unit, a flap identifying unit, a first synthesizing unit, an alignment processing unit and a second synthesizing unit. The image generating unit generates an echocardiographic image including an aorta. The acquiring unit acquires a heart area image including the aorta. The extracting unit extracts an artery region based on the heart area image. The flap identifying unit identifies a flap region based on the artery region. The first synthesizing unit synthesizes information on the flap region onto the artery region to generate a first synthesized image. The alignment processing unit performs processing to align an imaging region in the echocardiography on the heart area image based on a positional data signal. The second synthesizing unit synthesizes information that indicates the imaging region processed for alignment onto the first synthesized image to generate a second synthesized image.

9 Claims, 12 Drawing Sheets

(56) References Cited

U.S. PATENT DOCUMENTS

| | | | |
|---|---|---|---|
| 2008/0009733 A1* | 1/2008 | Saksena | 600/443 |
| 2008/0154102 A1* | 6/2008 | Frangioni et al. | 600/317 |
| 2008/0287777 A1* | 11/2008 | Li et al. | 600/424 |
| 2009/0130642 A1* | 5/2009 | Tada et al. | 434/262 |
| 2011/0229546 A1* | 9/2011 | Granville et al. | 424/423 |
| 2012/0157397 A1* | 6/2012 | Hazen et al. | 514/39 |

* cited by examiner

ULTRASONIC DIAGNOSTIC APPARATUS AND ULTRASONIC DIAGNOSIS ASSISTING METHOD

CROSS-REFERENCE TO RELATED APPLICATION

This application is based upon and claims the benefit of priority from Japanese Patent Application No. 2012-50926, filed on Mar. 7, 2012, the entire contents of which are incorporated herein by reference.

FIELD

An embodiment as one aspect of the present invention relates to an ultrasonic diagnostic apparatus and an ultrasonic diagnosis assisting method that display an echocardiographic image.

BACKGROUND

A largest artery that originates from a left ventricle of a heart, goes upward to form an aortic arch, and goes downward to end at a bifurcation of a common iliac artery is called an aorta. The aorta also serves as an originating source in blood circulation to an entire body. Similarly to other arteries, the aorta has a three-layer structure of an intima, a media, and an adventitia.

A condition called aortic dissection is one of the medical conditions pertaining to the aorta. The aortic dissection is a medical condition that is associated with severe pain caused by the aorta tearing into layers and that causes circulatory disturbance at a bifurcation. In the aortic dissection, a tear (an entry) appears in an intima, and as blood flows into the entry, the intima is separated, which leads to a double-lumen structure of a true lumen and a false lumen. The aortic dissection has a high mortality rate, and approximately 93% of the cases leads to death within 24 hours of onset.

A diagnosis of the aortic dissection can be made by using contrast imaging CT (computed tomography), MRI (magnetic resonance imaging), and ultrasound. Generally, the contrast imaging CT is used prior to an operation, and transesophageal echocardiography is used during an operation.

The aortic dissection is typically treated by removing the aorta including the torn region that has appeared in the intima and replacing with an artificial blood vessel. However, in the aortic dissection, the aorta may rapture while redoing CT imaging, and thus an operation is sometimes started without obtaining sufficient information for the pressing urgency.

In a case of a patient with a wide area of a flap (an intimal flap) that moves in accordance with pulsation, the entire flap may not be replaced with an artificial blood vessel depending on a physical strength of the patient. If that is the case, it is typical that only a region that is close to an aortic valve is replaced with an artificial blood vessel and the remaining region is treated through pharmacotherapy or the like. In such a case, even if a sufficient amount of blood is fed during the operation, the flap may block part of bifurcated arteries, which may lead to circulatory disturbance in organs beyond the blocked bifurcated arteries. In addition, a site of a flap may change, and thus, during the operation, it is necessary to proceed with the treatment while checking on the blood circulation in the aorta and the organs based on images from transesophageal echocardiography (TEE).

With an existing technique, there is a risk of overlooking a bifurcated artery that can be blocked by a flap during an operation for the aortic dissection using the transesophageal echocardiography. Furthermore, with an existing technique, there is a risk of overlooking circulatory disturbance that occurs at an unexpected location due to a flap moving within a range of a dissected intima during an operation for the aortic dissection using transesophageal echocardiography.

That is, with the existing techniques, a flap cannot be confirmed with high precision during an operation for the aortic dissection using transesophageal echocardiography.

BRIEF DESCRIPTION OF THE DRAWINGS

In accompanying drawings.

DETAILED DESCRIPTION

Figure 1:
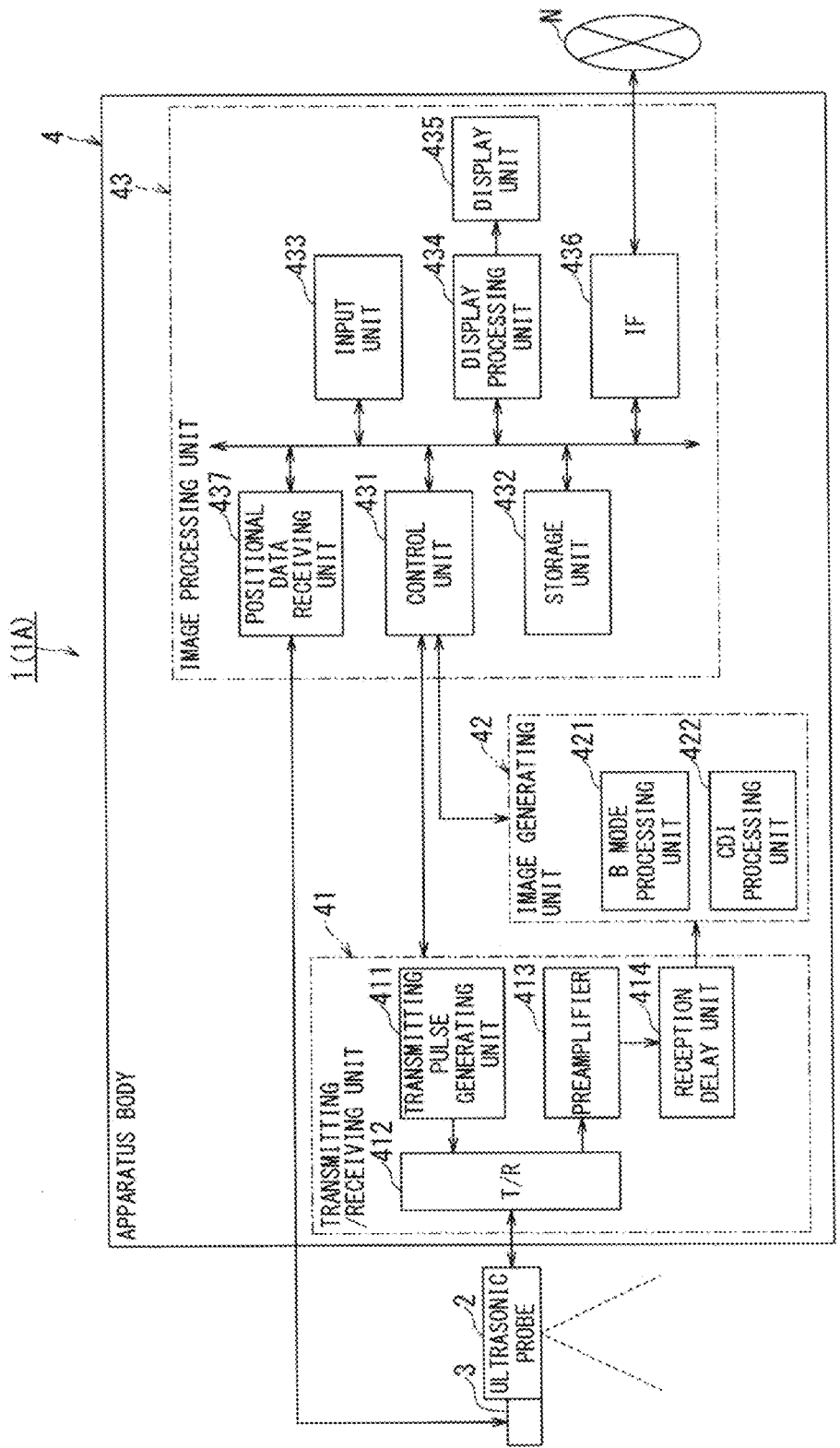
FIG. 1 is a schematic diagram showing a configuration of an ultrasonic diagnostic apparatus according to a first embodiment.

An ultrasonic diagnostic apparatus and an ultrasonic diagnosis assisting method according to the embodiments will be described with reference to the accompanying drawings.

To solve the above-described problems, the ultrasonic diagnostic apparatus according to the present embodiment includes: an image generating unit configured to control an ultrasonic probe to execute echocardiography and to generate an echocardiographic image including an aorta; a position sensor configured to generate a positional data signal pertaining to a spatial coordinate position and a scanning direction/orientation; an acquiring unit configured to acquire a heart area image including the aorta; an extracting unit configured to extract an artery region based on the heart area image; a flap identifying unit configured to identify a flap region based on the artery region; a first synthesizing unit configured to synthesize information on the flap region onto the artery region to generate a first synthesized image; an alignment processing unit configured to perform processing to align an imaging region in the echocardiography on the heart area image based on the positional data signal; and a second synthesizing unit configured to synthesize information that indicates the imaging region processed for alignment onto the first synthesized image to generate a second synthesized image.

To solve the above-described problems, the ultrasonic diagnostic apparatus according to the present embodiment includes: an image generating unit configured to control an ultrasonic probe to execute echocardiography and to generate an echocardiographic image including an aorta; a position sensor configured to generate a positional data signal pertaining to a spatial coordinate position and a scanning direction/orientation; an acquiring unit configured to acquire a heart area image including the aorta; an extracting unit configured to extract an artery region based on the heart area image; a flap identifying unit configured to identify a flap region based on the artery region; a first synthesizing unit configured to synthesize information on the flap region onto the artery region to generate a first synthesized image; an alignment processing unit configured to perform processing to align an imaging region in the echocardiography on the heart area image based on the positional data signal; a registering unit configured to register the imaging region processed for alignment in a storage together with an imaging time; a measuring unit configured to measure an elapsed time since a final imaging time for each portion of the heart area image based on the previous imaging region and the registered previous imaging time; and a second synthesizing unit configured to generate a second synthesized image that indicates information based on the elapsed time on the first synthesized image.

To solve the above-described problems, the ultrasonic diagnosis assisting method according to the present embodiment includes: controlling an ultrasonic probe to execute echocardiography and generating an echocardiographic image including an aorta; acquiring a heart area image including the aorta from a storage; extracting an artery region based on the heart area image; identifying a flap region based on the artery region; synthesizing information on the flap region onto the artery region to generate a first synthesized image; performing processing to align an imaging region in the echocardiography on the heart area image based on a positional data signal pertaining to a spatial coordinate position and a scanning direction/orientation; synthesizing information that indicates the imaging region processed for alignment onto the first synthesized image to generate a second synthesized image; and displaying the second synthesized image on a display.

To solve the above-described problems, the ultrasonic diagnosis assisting method according to the present embodiment includes: controlling an ultrasonic probe to execute echocardiography and generating an echocardiographic image including an aorta; acquiring a heart area image including the aorta from a first storage; extracting an artery region based on the heart area image; identifying a flap region based on the artery region; synthesizing information on the flap region onto the artery region to generate a first synthesized image; performing processing to align an imaging region in the echocardiography on the heart area image based on a positional data signal pertaining to a spatial coordinate position and a scanning direction/orientation; registering the imaging region processed for alignment in a second storage together with an imaging time; measuring an elapsed time since a final imaging time for each portion of the heart area image based on the previous imaging region and the registered previous imaging time; generating a second synthesized image that indicates information based on the elapsed time on the first synthesized image; and displaying the second synthesized image on a display.

First Embodiment

FIG. 1 is a schematic diagram showing a configuration of an ultrasonic diagnostic apparatus according to a first embodiment.

FIG. 1 shows an ultrasonic diagnostic apparatus 1 of the first embodiment. The ultrasonic diagnostic apparatus 1 includes an ultrasonic probe 2, a position sensor 3, and an apparatus body 4.

The ultrasonic probe 2 is used in echocardiography in which the ultrasonic probe 2 makes contact with a surface of a body of an object (not shown) to transmit and receive ultrasonic waves from an outside of the object. Alternatively, the ultrasonic probe 2 is used in transesophageal echocardiography (TEE) in which the ultrasonic probe 2 transmits and receives ultrasonic waves inside an object (not shown). Hereinafter, descriptions are given assuming that the ultrasonic probe 2 is used in transesophageal echocardiography.

The ultrasonic probe 2 is configured of a plurality of ultrasonic transducers (piezoelectric elements) that are arranged linearly or in a two-dimensional array. Each of the ultrasonic transducers is driven under the control of the apparatus body 4 and scans an object (a site) with an ultrasonic beam that accords with a transmitting beamforming condition that is set in advance. Further, each of the ultrasonic transducers receives an ultrasonic echo signal that returns to the ultrasonic probe 2 as the ultrasonic beam is reflected at an acoustic impedance boundary in the object or is scattered by a minute scatterer to convert the ultrasonic echo signal into an echo signal of a weak voltage and transmits the converted signal to the apparatus body 4.

The position sensor 3 is attached to the ultrasonic probe 2. The position sensor 3 generates a positional data signal that pertains to a spatial coordinate position and a scanning direction/orientation and transmits the positional data signal to the apparatus body 4.

The apparatus body 4 includes a transmitting/receiving unit 41, an image generating unit 42, and an image processing unit 43.

The transmitting/receiving unit 41 of the apparatus body 4 transmits and receives an electric signal to and from the ultrasonic probe 2 in accordance with the control of the image processing unit 43. The transmitting/receiving unit 41 includes a transmitting pulse generating unit 411, a T/R (transmitter/receiver) 412, a preamplifier 413, and a reception delay unit 414.

The transmitting pulse generating unit 411 generates a pulse voltage to control a direction and a convergence of the ultrasonic beam from the ultrasonic probe 2 based on a transmitting beamforming condition that is set in advance.

The T/R 412 supplies a drive signal that is based on the pulse voltage generated by the transmitting pulse generating unit 411 to the ultrasonic probe 2 through the transmitter. Further, the T/R 412 receives the received signal from the ultrasonic probe 2.

The preamplifier 413 amplifies the received signal that has been received through the receiver of the T/R 412 and transmits an amplified signal to the reception delay unit 414.

The reception delay unit 414 is connected to an output side of the preamplifier 413. The reception delay unit 414 includes a plurality of beamformers that are capable of receiving received signals from the preamplifier 413 in parallel and simultaneously. In each of the beamformers, a reception delay is applied to each received signal to satisfy a condition concerning a direction and a convergence of the ultrasonic beam in the receiving beamforming that is set in advance. The reception delay unit 414 supplies a delayed signal to the image generating unit 42 in a subsequent stage.

The image generating unit 42 of the apparatus body 4 performs signal processing on a received signal from the transmitting/receiving unit 41 in accordance with the control of the image processing unit 43. The image generating unit 42 includes a B mode processing unit 421 and a CDI (color Doppler imaging) processing unit 422. The image generating unit 42 may be configured to generate a Doppler spectrum. B mode data and CDI data that are generated by the image generating unit 42 are synthesized as necessary and sent to the image processing unit 43. Then, these data are displayed as a transesophageal echocardiographic image (transesophageal echocardiographic image data) in the image processing unit 43.

The B mode processing unit 421 performs quadrature detection on a received signal from the reception delay unit 414 using a predetermined reference frequency in accordance with the control of a control unit 431 and generates B mode data in accordance with signal amplitude of a detected signal. Further, the B mode processing unit 421 sequentially saves B mode data that are generated per scanning direction to generate the B mode data. The B mode data are converted into a scanning line signal array of a video format to be sent to the image processing unit 43.

The CDI processing unit 422 measures a change over time in a phase with respect to the received signal from the reception delay unit 414, to thereby generate CDI data that are based on speed, power, dispersion, and the like that indicate information on blood flow in an object. Further, the CDI processing unit 422 sequentially saves CDI data that are generated per scanning direction to generate the CDI data. The CDI data are converted into a scanning line signal array of a video format to be sent to the image processing unit 43.

The image processing unit 43 of the apparatus body 4 includes the control unit 431, a storage unit 432, an input unit 433, a display processing unit 434, a display unit 435, an IF 436, and a positional data receiving unit 437.

The control unit 431 includes a CPU (central processing unit) (not shown) and an internal storage device (not shown). The CPU is a control device having a configuration of an integrated circuit (LSI), in which an electronic circuit configured of a semiconductor is enclosed in a package that has a plurality of terminals. The internal storage device is a storage device that includes components such as a ROM (read only memory) and a RAM (random access memory). The control unit 431 controls operations of the transmitting/receiving unit 41 and the image generating unit 42 and operations of the storage unit 432, the input unit 433, the display processing unit 434, the IF 436, and the positional data receiving unit 437 of the image processing unit 43.

The internal storage device of the control unit 431 has a function of storing data or being used to temporarily store work memory of the CPU and data. The control unit 431 controls each unit through a bus.

The storage unit 432 stores image data outputted from the image generating unit 42, positional data, which will be described later, and so forth in accordance with the control of the control unit 431.

The input unit 433 is connected to the control unit 431. The input unit 433 is provided with an input device such as a joystick and a trackball, through which various settings pertaining to the transmitting/receiving conditions of the ultrasonic beam are set/modified (examples of the input device also include a switch, various buttons, and a keyboard). Information instructed by an operator operating the input unit 433 is sent to the control unit 431. Through this, settings in each unit of the apparatus body 4 are set/modified.

The display processing unit 434 causes synthesized data of the B mode data and the CDI data sent from the image generating unit 42 to be displayed on the display unit 435 as a transesophageal echocardiographic image in accordance with the control of the control unit 431. Further, the display processing unit 434 causes a synthesized image, which will be described later, to be displayed on the display unit 435 in accordance with the control of the control unit 431.

The display unit 435 displays data outputted from the display processing unit 434 along with character information of various parameters, scales, and so forth.

The IF 436 is configured of connectors that are compatible with parallel connection specifications and serial connection specifications and performs a communication control in accordance with each standard. The IF 436 has a function of being capable of connecting to a network N, and thus the ultrasonic diagnostic apparatus 1 can connect to the network N via the IF 436.

The positional data receiving unit 437 receives a positional data signal that is generated by the position sensor 3.

Figure 2:
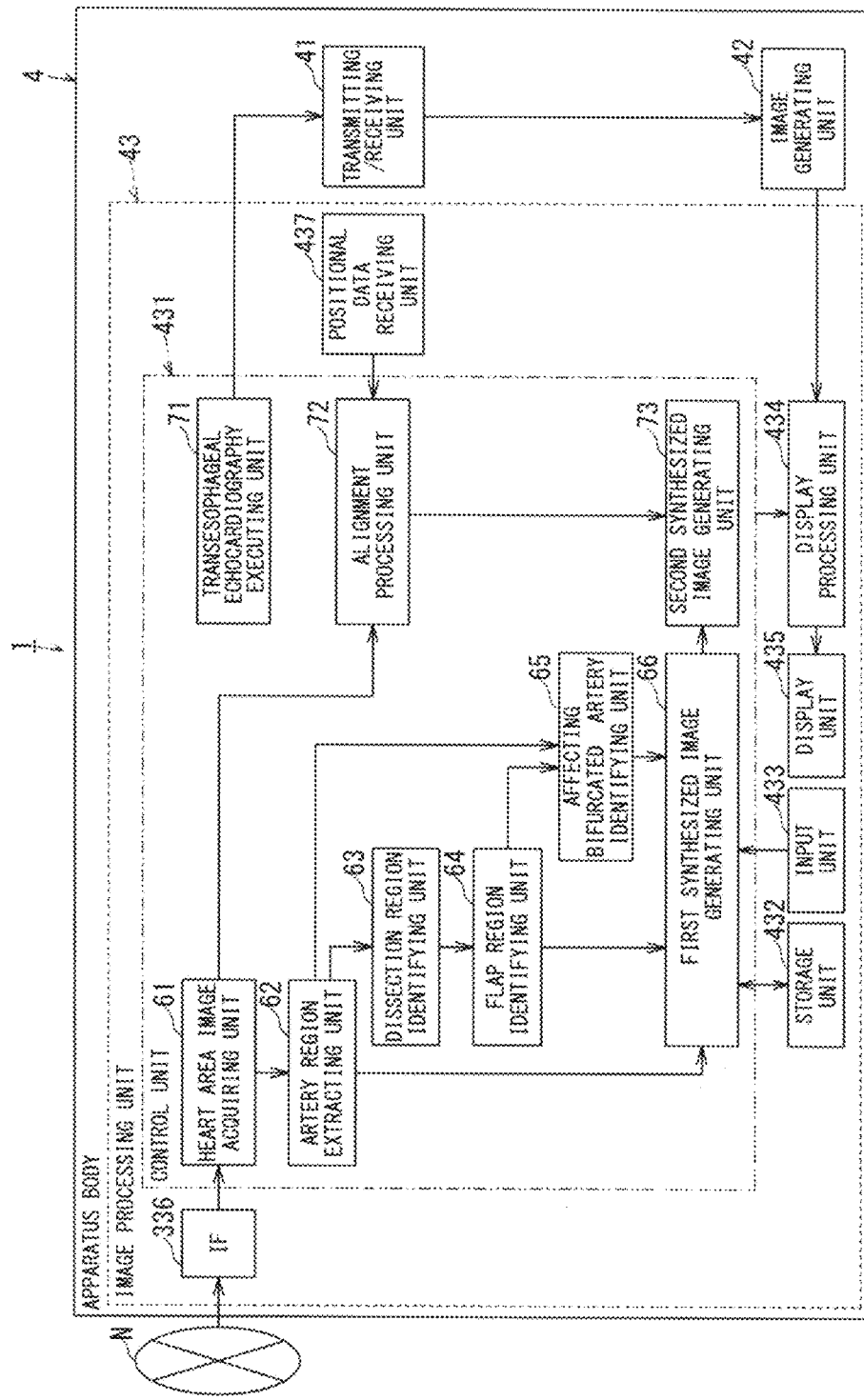
FIG. 2 is a block diagram showing functions of the ultrasonic diagnostic apparatus according to the first embodiment.

FIG. 2 is a block diagram showing functions of the ultrasonic diagnostic apparatus 1 according to the first embodiment.

As the control unit 431 shown in FIG. 1 executes a program, the ultrasonic diagnostic apparatus 1 functions as a heart area image acquiring unit 61, an artery region extracting unit 62, a dissection region identifying unit 63, a flap region identifying unit 64, an affecting bifurcated artery identifying unit 65, a first synthesized image generating unit 66, a transesophageal echocardiography executing unit 71, an alignment processing unit 72, and a second synthesized image generating unit 73, as shown in FIG. 2. Although it is stated that each of the units 61 to 66 and 71 to 73 that constitute the ultrasonic diagnostic apparatus 1 functions as the program is executed, the present invention is not limited to that case. All or part of the units 61 to 66 and 71 to 73 that constitute the ultrasonic diagnostic apparatus 1 may be provided as hardware in the ultrasonic diagnostic apparatus 1.

Each of the units 61 to 66 that constitute the ultrasonic diagnostic apparatus 1 functions prior to executing transesophageal echocardiography, whereas each of the units 71 to 73 that constitute the ultrasonic diagnostic apparatus 1 functions during an operation for the aortic dissection using transesophageal echocardiography.

The heart area image acquiring unit 61 has a function of acquiring, from the network N (an image server or the like) through an IF 336, a heart area image (heart area image data) that includes the aorta (an ascending aorta, an aortic arch, and a descending aorta) around the heart of the object and bifurcated arteries (a brachiocephalic artery (BCA), a left common carotid artery (LCA), a left subclavian artery (LSCA), and so forth) that bifurcate from the aorta. For example, the heart area image acquiring unit 61 acquires a heart area image that is based on MR angiography (MRA) in contrast imaging or noncontrast imaging or CT angiography (CTA). The heart area image acquiring unit 61 acquires heart area images of a plurality of time phases (e.g., end-diastolic and end-systolic phases). Note that the heart area image acquiring unit 61 may also acquire a heart area image of a region that includes a thoracoabdominal aorta and an abdominal aorta around the heart of the object, a bifurcated artery (a posterior intercostal artery) that bifurcates from the thoracoabdominal aorta, bifurcated arteries (a renal artery, a celiac artery, and a mesenteric artery) that bifurcate from the abdominal aorta.

The artery region extracting unit 62 has a function of extracting an artery region (artery region data) based on the heart area image acquired by the heart area image acquiring unit 61. The artery region extracting unit 62 extracts the artery region through a publicly known technique or based on a region, which is inputted through the input unit 433, in the heart area image displayed on the display unit 435. As an existing technique, segmentation processing can, for example, be cited.

Figure 3:
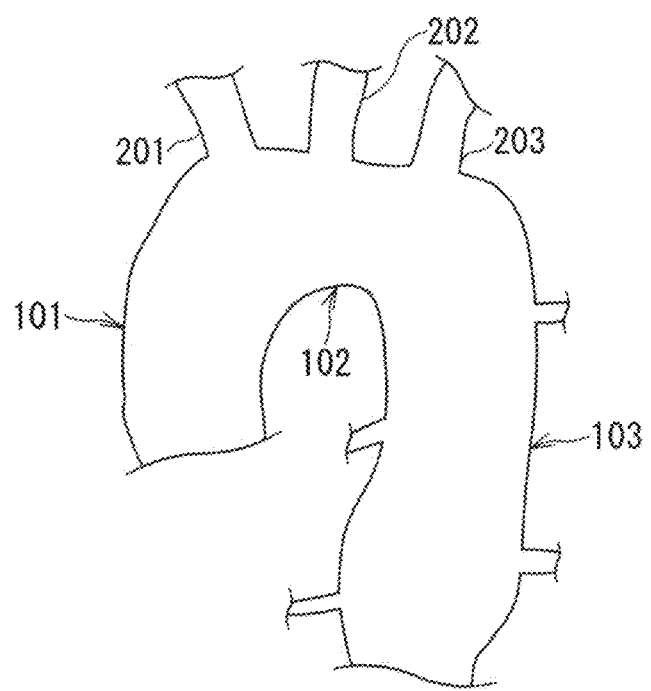
FIG. 3 is a diagram showing an example of an artery region.

FIG. 3 is a diagram showing an example of an artery region.

FIG. 3 is a diagram showing an artery region that is included in a heart area image in a case where an aortic dissection has occurred. As shown in FIG. 3, the artery region includes an ascending aorta region 101 of an aorta around the heart, an aortic arch region 102 of the aorta, and a descending aorta region 103 of the aorta. The artery region also includes a BCA region 201 as a bifurcated artery region that bifurcates from the aortic arch region 102, an LCA region 202 also as a bifurcated artery from the aortic arch region 102, and an LSCA region 203 also as a bifurcated artery from the aortic arch region 102. The artery region further includes bifurcated arteries that bifurcate from the descending aorta region 103.

Referring back to FIG. 2, the dissection region identifying unit 63 has a function of identifying a true lumen region (true lumen region data) within an aorta region, a false lumen region (false lumen region data), and a dissected intima region (dissected intima region data) that is an intima region that has been dissected, respectively.

FIGS. 4A to 4E are diagrams to illustrate a method for identifying each region.

Figure 4A:
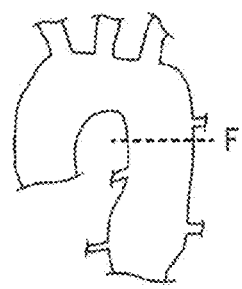
FIGS. 4A to 4E are diagrams to illustrate a method for identifying each region.

FIG. 4A is a diagram showing an artery region that is included in a heart area image in a case where an aortic dissection has occurred. As shown in FIG. 4A, one aorta section F (a section orthogonal to a core of the aorta) is selected based on the artery region.

FIGS. 4B to 4E are sectional views along the aorta section F shown in FIG. 4A.

Figure 4B:
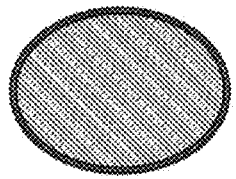
Figure 4C:
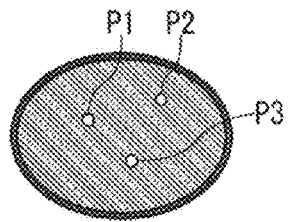

As shown in FIG. 4C, clustering is performed on the artery region along the aorta section F shown in FIG. 4B. For example, three clusters A1, A2, and A3 (shown in FIGS. 4D and 4E) are obtained through a k-means method in which three control points (representative points of the clusters) P1, P2, and P3 are initially arranged in the artery region along the aorta section F. If pixel values of the three clusters A1, A2, and A3 are substantially the same as one another (within a threshold), it is determined that the artery is not dissected in the aorta section F. On the other hand, if pixel values of the three clusters A1, A2, and A3 are different from one another (exceeding a threshold), it is determined that the artery is dissected in the aorta section F. Then, the two clusters A1 and A2 having high pixel values are determined as true lumen and false lumen regions, whereas the cluster A3 having a low pixel value is determined as a flap region of the dissected intima.

Furthermore, the cluster A1 that is inputted as a true lumen through the input unit 433 is determined as the true lumen region, and the cluster A2 that is similarly inputted as a false lumen is determined as the false lumen region. Alternatively, the cluster A1 in an aorta section F that lies along an extension of a true lumen in an aorta section that is another part of an artery portion and that does not include a false lumen is determined as the true lumen region, whereas the cluster F2 in the aorta section F is determined as the false lumen.

In a case where an aortic dissection has occurred, in addition to a true lumen, a false lumen is present in an artery in the aorta section F. When a weak portion of an aortic wall is subjected to a stress and a part of the intima is torn, blood in the lumen enters into medial tissues (an entry of the dissection). Since the medial tissues are sponge-like, the medial tissues are easily broken and dissected. Then, the blood successively flows into the broken medial tissues, which leads to a state shown in FIG. 4D, which includes the true lumen region A1, the false lumen region A2, and the dissected intima region A3. Here, the adventitia is also pressurized. As the dissection further progresses, the condition progresses from the state shown in FIG. 4D to the state shown in FIG. 4E.

Figure 4D:
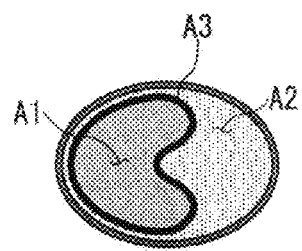
Figure 4E:
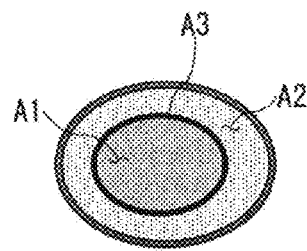

Furthermore, the true lumen region A1, the false lumen region A2, and the dissected intima region A3 of the entire aorta are identified using a region growing method based on positional information of the true lumen region A1, the false lumen region A2, and the dissected intima region A3 shown in FIGS. 4D and 4E. Alternatively, the clustering is executed on the entire aorta to identify the true lumen region A1, the false lumen region A2, and the dissected intima region A3 of the entire aorta.

Figure 5A:
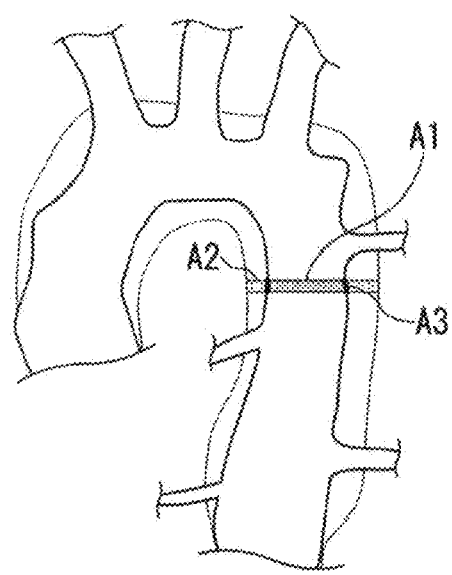
FIGS. 5A and 5B are diagrams to illustrate a method for identifying regions of the entire aorta.
Figure 5B:
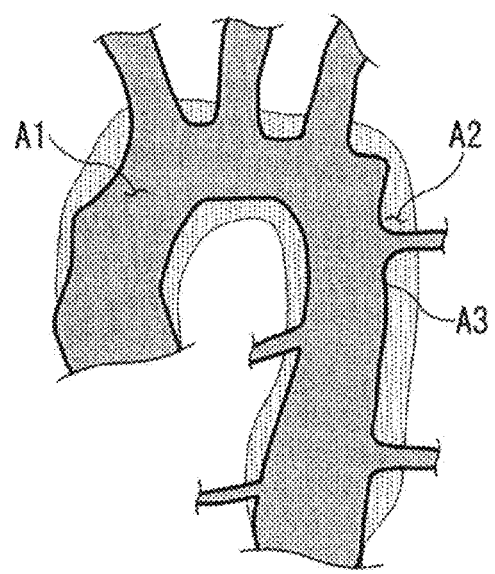

FIGS. 5A and 5B are diagrams to illustrate a method for identifying regions of the entire aorta.

FIGS. 5A and 5B are diagrams showing an artery region that is included in a heart area image in a case where an aortic dissection has occurred.

FIG. 5A shows the true lumen region A1, the false lumen region A2, and the dissected intima region A3 that are identified in a single section, as described using FIG. 4E. Processing through the region growing method is performed based on the positional information of the true lumen region A1, the false lumen region A2, and the dissected intima region A3 shown in FIG. 5A. Processing through the region growing method yields a result as shown in FIG. 5B.

Referring back to FIG. 2, the flap region identifying unit 64 has a function of identifying a flap region that fluctuates in accordance with pulsation, based on the artery region that has been extracted by the artery region extracting unit 62. The flap region identifying unit 64 is suitable for identifying a flap region (flap region data) based on the dissected intima region that has been identified within the artery region by the dissection region identifying unit 63. The flap region is a region of the dissected intima region that fluctuates in accordance with pulsation.

Figure 6:
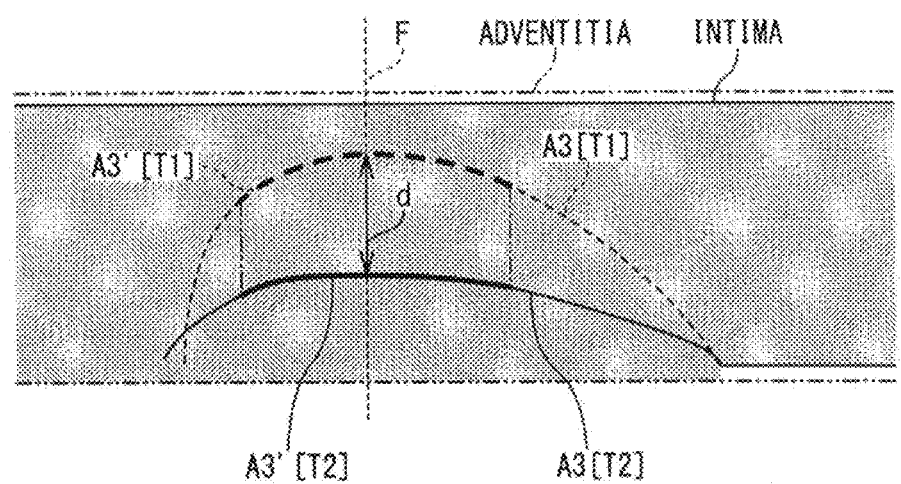
FIG. 6 is a diagram to illustrate a method for identifying a flap region.

FIG. 6 is a diagram to illustrate a method for identifying a flap region.

FIG. 6 is a longitudinal sectional view showing an artery region in a case where an aortic dissection has occurred and a flap region is present in the aorta section F shown in FIG. 4A.

A dissected intima region A3[T1] of a first time phase and a dissected intima region A3[T2] of a second time phase are extracted based on a difference image of a dissected intima region that is based on an artery region of the first time phase and of a dissected intima region that is based on an artery region of the second time phase. Then, regions where a distance d between the dissected intima region A3[T1] and the dissected intima region A3[T2] along the core of the artery is equal to or greater than a threshold are identified as flap regions A3'[T1] and A3'[T2], respectively.

Although a case where the flap region identifying unit 64 identifies the flap region based on the dissected intima region has been described, the present invention is not limited to that case. For example, the flap region identifying unit 64 may identify a flap region based on an artery region.

Referring back to FIG. 2, the affecting bifurcated artery identifying unit 65 has a function of identifying a bifurcated artery that affects blood circulation (where there is a possibility that circulatory disturbance occurs) as an affecting bifurcated artery, based on the artery region that has been extracted by the artery region extracting unit 62 and the flap region that has been identified by the flap region identifying unit 64.

Figure 7:
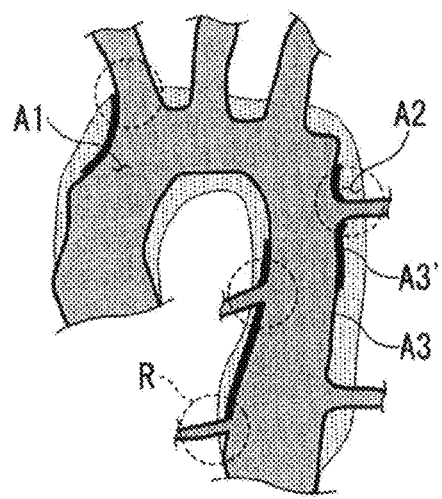
FIG. 7 is a diagram to illustrate a method for identifying an affecting bifurcated artery.

FIG. 7 is a diagram to illustrate a method for identifying an affecting bifurcated artery.

FIG. 7 is a diagram showing an artery region that is included in a heart area image in a case where an aortic dissection has occurred.

As shown in FIG. 7, an affecting bifurcated artery is identified as bifurcated arteries that are present within a predetermined distance R from the flap region A3' (the flap region A3'[T1] or the flap region A3'[T2] shown in FIG. 6) are searched for. Alternatively, in a case where the flap region A3' is present within a predetermined distance from an intersection, serving as a center, of the core of the aorta and a core of an bifurcated artery, that bifurcated artery is identified as an affecting bifurcated artery.

Referring back to FIG. 2, the first synthesized image generating unit 66 has a function of synthesizing information on the flap region that has been identified by the flap region identifying unit 64 and information on the affecting bifurcated artery that has been identified by the affecting bifurcated artery identifying unit 65 onto the artery region that has been extracted by the artery region extracting unit 62 to generate a first synthesized image (first synthesized image data). For example, the first synthesized image generating unit 66 synthesizes information that indicates the presence of the flap region onto a relevant portion of the false lumen, within the artery region, that has been identified by the dissection region identifying unit 63 to generate the first synthesized image. The first synthesized image that has been generated by the first synthesized image generating unit 66 is displayed on the display unit 435 through the display processing unit 434.

Figure 8:
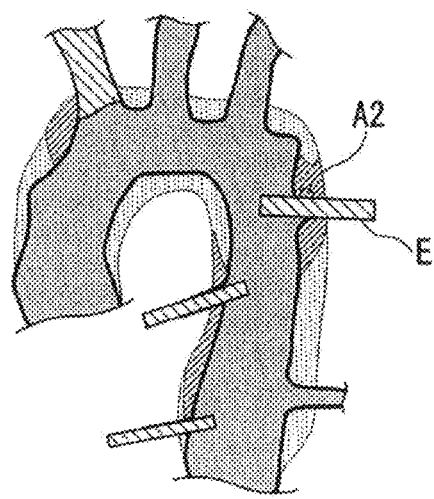
FIG. 8 is a diagram showing an example of a first synthesized image in the ultrasonic diagnostic apparatus according to the first embodiment.

FIG. 8 is a diagram showing an example of the first synthesized image in the ultrasonic diagnostic apparatus 1 according to the first embodiment.

FIG. 8 is a diagram showing a first synthesized image in a case where an aortic dissection has occurred and a flap region is present.

FIG. 8 shows the first synthesized image in which information that indicates the presence of the flap region A3' is synthesized onto a relevant portion (a relevant position) in the false lumen region A2 of the artery region and information that indicates an affecting bifurcated artery E that is based on the presence of the flap region A3' is synthesized thereon. As shown in FIG. 8, whether or not the flap region is present in the artery region and whether or not the affecting bifurcated artery E that is based on the flap region is present can be visually recognized in the first synthesized image.

Referring back to FIG. 2, the transesophageal echocardiography executing unit 71 has a function of causing the transmitting/receiving unit 41 and the image generating unit 42 to operate in accordance with an instruction inputted through the input unit 433 to execute transesophageal echocardiography on a region that includes an aorta around the heart of the object and a bifurcated artery that bifurcates from the aorta, to thereby obtain a transesophageal echocardiographic image.

The alignment processing unit 72 has a function of aligning an imaging region in transesophageal echocardiography with the heart area image that has been acquired by the heart area image acquiring unit 61, based on a positional data signal received by the positional data receiving unit 437. The alignment processing unit 72 calculates the imaging region in transesophageal echocardiography on the heart area image in accordance with a publicly known technique.

The second synthesized image generating unit 73 has a function of synthesizing information that indicates the imaging region in transesophageal echocardiography that has been acquired by the alignment processing unit 72 onto the first synthesized image that has been generated by the first synthesized image generating unit 66 to generate a second synthesized image (second synthesized image data). The second synthesized image generating unit 73 may generate the second synthesized image as a partial image of in the imaging region in transesophageal echocardiography that has been acquired by the alignment processing unit 72, of the first synthesized image that has been generated by the first synthesized image generating unit 66. The second synthesized image that has been generated by the second synthesized image generating unit 73 is displayed on the display unit 435 through the display processing unit 434.

Figure 9:
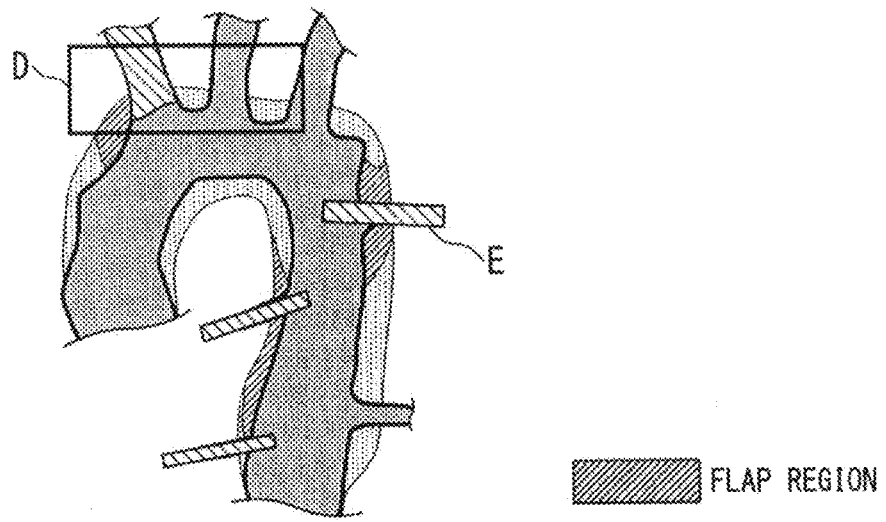
FIG. 9 is a diagram showing an example of a second synthesized image in the ultrasonic diagnostic apparatus according to the first embodiment.

FIG. 9 is a diagram showing an example of the second synthesized image in the ultrasonic diagnostic apparatus 1 according to the first embodiment.

FIG. 9 is a diagram showing a second synthesized image in a case where an aortic dissection has occurred and a flap region is present. FIG. 9 shows the second synthesized image in which information that indicates an imaging region D in transesophageal echocardiography is synthesized onto the first synthesized image. As shown in FIG. 9, whether or not the flap region is present in the artery region and whether or not the affecting bifurcated artery E that is based on the flap region is present can be visually recognized in the imaging region D in transesophageal echocardiography on the second synthesized image.

Although a case where the affecting bifurcated artery identifying unit 65 shown in FIG. 2 identifies the affecting bifurcated artery based on the flap region has been described, the present invention is not limited to that case. For example, the affecting bifurcated artery identifying unit 65 may identify an affecting bifurcated artery based on a dissected intima region. That case will be described using FIGS. 10 to 12.

Figure 10:
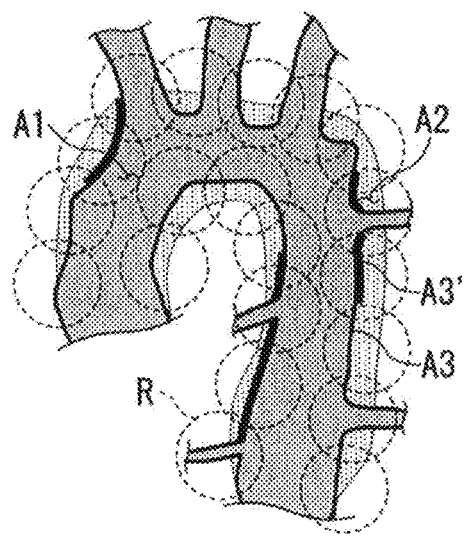
FIG. 10 is a diagram to illustrate a method for identifying an affecting bifurcated artery.

FIG. 10 is a diagram to illustrate a method for identifying an affecting bifurcated artery. FIG. 10 corresponds to FIG. 7.

FIG. 10 is a diagram showing an artery region that is included in a heart area image in a case where an aortic dissection has occurred.

As shown in FIG. 10, an affecting bifurcated artery is identified as bifurcated arteries that are present within a predetermined distance R from the dissected intima region A3 are searched for. Alternatively, in a case where the dissected intima region A3 is present within a predetermined distance from an intersection, serving as a center, of the core of the aorta and the core of a bifurcated artery, that bifurcated artery is identified as an affecting bifurcated artery.

Figure 11:
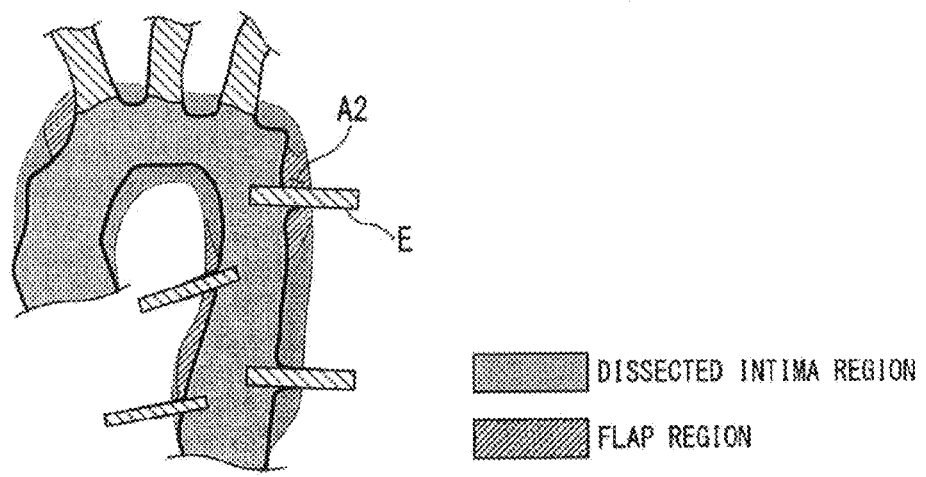
FIG. 11 is a diagram showing an example of a first synthesized image in the ultrasonic diagnostic apparatus according to the first embodiment.

FIG. 11 is a diagram showing an example of the first synthesized image in the ultrasonic diagnostic apparatus 1 according to the first embodiment. FIG. 11 corresponds to FIG. 8.

FIG. 11 is a diagram showing a first synthesized image in a case where an aortic dissection has occurred and a flap region is present.

FIG. 11 shows the first synthesized image in which information that indicates the presence of the dissected intima region A3 and the flap region A3' is synthesized onto a relevant portion (a relevant position) in the false lumen region A2 of the artery region and information that indicates the affecting bifurcated artery E that is based on the presence of the dissected intima region A3 is synthesized thereon. As shown in FIG. 11, whether or not the flap region is present in the artery region and whether or not the affecting bifurcated artery E that is based on the dissected intima region is present can be visually recognized in the first synthesized image. As the affecting bifurcated artery E is identified based on the dissected intima region, a range in which the flap moves within a range of the dissected intima can be estimated.

Figure 12:
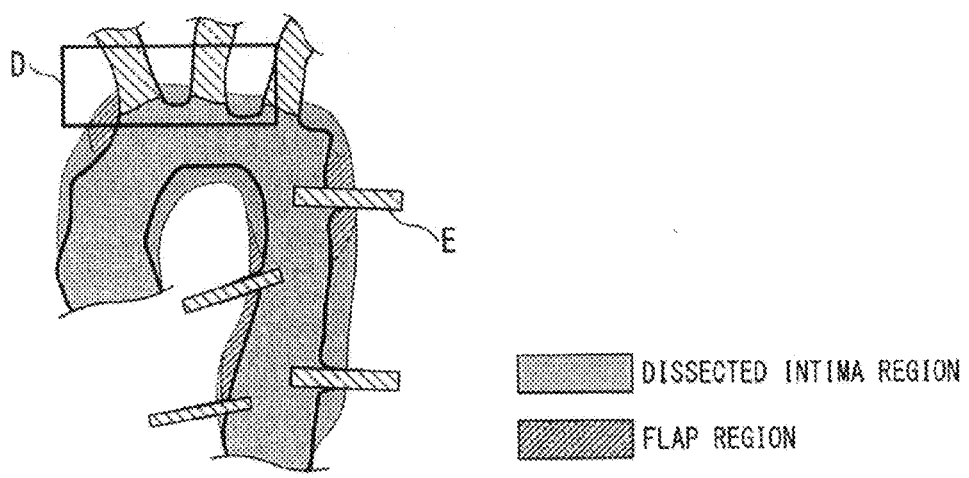
FIG. 12 is a diagram showing an example of a second synthesized image in the ultrasonic diagnostic apparatus according to the first embodiment.

FIG. 12 is a diagram showing an example of the second synthesized image in the ultrasonic diagnostic apparatus 1 according to the first embodiment. FIG. 12 corresponds to FIG. 9.

FIG. 12 is a diagram showing a second synthesized image in a case where an aortic dissection has occurred and a flap region is present. FIG. 12 shows the second synthesized image in which information that indicates the imaging region D in transesophageal echocardiography is synthesized onto the first synthesized image. As shown in FIG. 12, whether or not the flap region is present in the artery region and whether or not the affecting bifurcated artery E that is based on the dissected intima region is present can be visually recognized in the imaging region D in transesophageal echocardiography on the second synthesized image.

According to the ultrasonic diagnostic apparatus 1 of the first embodiment, whether or not a flap is present in an aorta within an imaging region in transesophageal echocardiography and whether or not a bifurcated artery that is affected by a flap is present can be visually recognized during an operation for an aortic dissection using transesophageal echocardiography. That is, a bifurcated artery that may be blocked by a flap can be prevented from being overlooked. Accordingly, according to the ultrasonic diagnostic apparatus 1 of the first embodiment, a flap can be confirmed with high precision during an operation for an aortic dissection using transesophageal echocardiography.

Furthermore, according to the ultrasonic diagnostic apparatus 1 of the first embodiment, whether or not a bifurcated artery that is affected is present in a dissected intima region can be visually recognized during an operation for an aortic dissection using echocardiography. That is, a risk where circulatory disturbance at an unexpected location caused by a flap moving within a range of the dissected intima is overlooked is eliminated. Accordingly, according to the ultrasonic diagnostic apparatus 1 of the first embodiment, a flap can be confirmed with high precision during an operation for an aortic dissection using echocardiography.

Second Embodiment

An overall configuration of an ultrasonic diagnostic apparatus 1A according to a second embodiment is the same as the configuration of the ultrasonic diagnostic apparatus 1 according to the first embodiment shown in FIG. 1, and thus the description thereof will be omitted.

Figure 13:
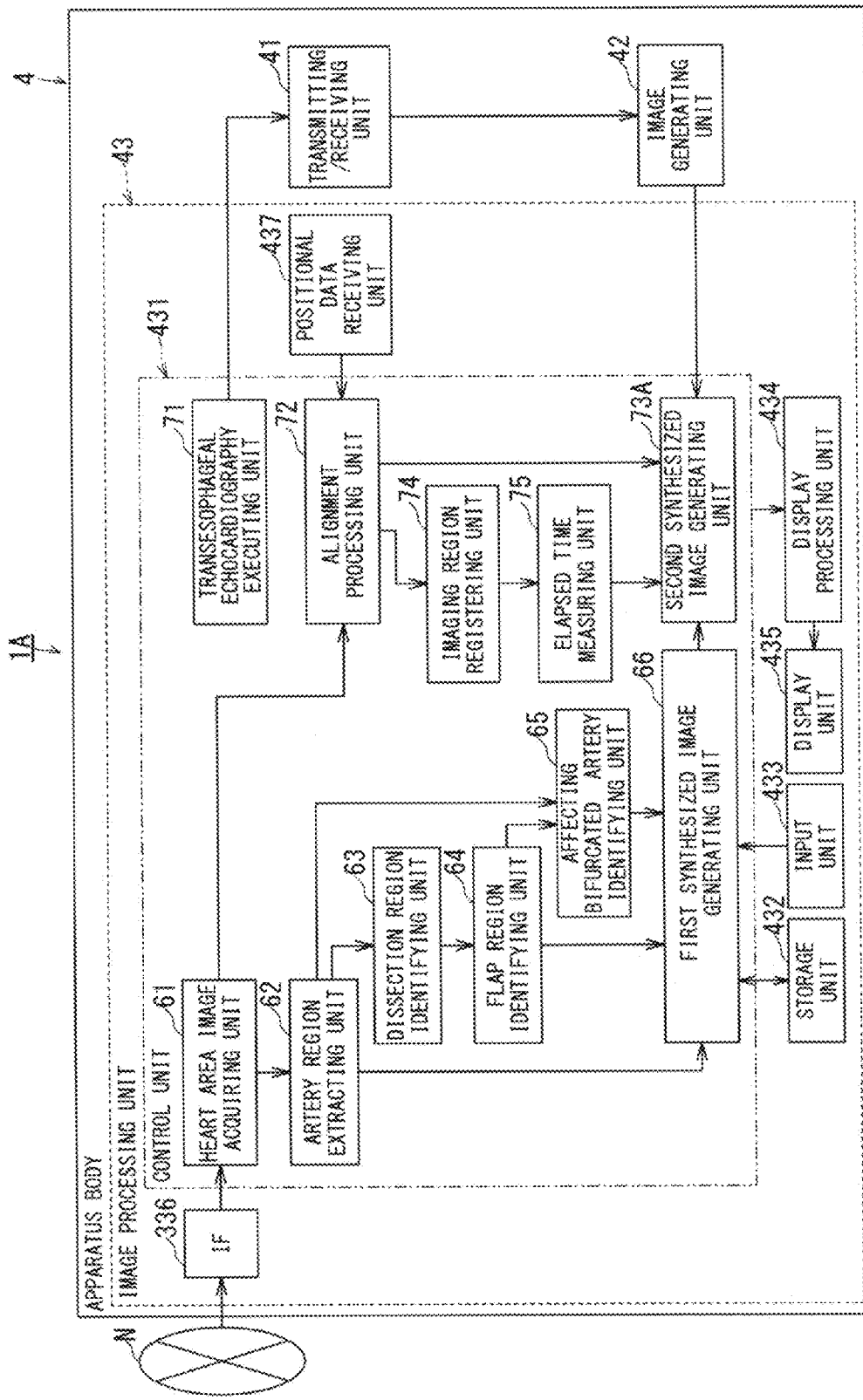
FIG. 13 is a block diagram showing functions of an ultrasonic diagnostic apparatus according to a second embodiment.

FIG. 13 is a block diagram showing functions of the ultrasonic diagnostic apparatus 1A according to the second embodiment.

The ultrasonic diagnostic apparatus 1A of the second embodiment shown in FIG. 13 includes, in addition to the components of the ultrasonic diagnostic apparatus 1 of the first embodiment shown in FIG. 2, an imaging region registering unit 74 and an elapsed time measuring unit 75.

As the control unit 431 shown in FIG. 1 executes a program, the ultrasonic diagnostic apparatus 1A functions as the heart area image acquiring unit 61, the artery region extracting unit 62, the dissection region identifying unit 63, the flap region identifying unit 64, the affecting bifurcated artery identifying unit 65, the first synthesized image generating unit 66, the transesophageal echocardiography executing unit 71, the alignment processing unit 72, a second synthesized image generating unit 73A, the imaging region registering unit 74, and the elapsed time measuring unit 75, as shown in FIG. 13. Although it is stated that each of the units 61 to 66 and 71 to 75 that constitute the ultrasonic diagnostic apparatus 1A functions as the program is executed, the present invention is not limited to that case. All or part of the units 61 to 66 and 71 to 75 that constitute the ultrasonic diagnostic apparatus 1A may be provided as hardware in the ultrasonic diagnostic apparatus 1A.

Each of the units 61 to 66 that constitute the ultrasonic diagnostic apparatus 1A functions prior to executing transesophageal echocardiography, whereas each of the units 71 to 75 that constitute the ultrasonic diagnostic apparatus 1A functions during an operation for an aortic dissection using transesophageal echocardiography. In the ultrasonic diagnostic apparatus 1A shown in FIG. 13, functions that are identical to those in the ultrasonic diagnostic apparatus 1 shown in FIG. 2 are given the identical reference characters, and the description thereof will be omitted.

The imaging region registering unit 74 has a function of registering an imaging region in transesophageal echocardiography on a heart area image that has been processed for alignment by the alignment processing unit 72 in the storage unit 432 together with an imaging time.

The elapsed time measuring unit 75 has a function of acquiring the imaging region and the imaging time of a previous instance of transesophageal echocardiography on the heart area image that have been registered in the storage unit 432 by the imaging region registering unit 74 and measuring time that elapses since a final ultrasonic imaging time for each portion of the heart area image.

The second synthesized image generating unit 73A has a function of generating the second synthesized image, in which information that is based on an elapsed time measured by the elapsed time measuring unit 75 is indicated on the first synthesized image that has been generated by the first synthesized image generating unit 66. The second synthesized image generating unit 73A may generate the second synthesized image in which the imaging region of a current instance of transesophageal echocardiography that has been acquired by the alignment processing unit 72 and information that is based on the imaging region and the elapsed time of a previous instance of transesophageal echocardiography are indicated on the first synthesized image that has been generated by the first synthesized image generating unit 66. The second synthesized image that has been generated by the second synthesized image generating unit 73A is displayed on the display unit 435 through the display processing unit 434.

Figure 14:
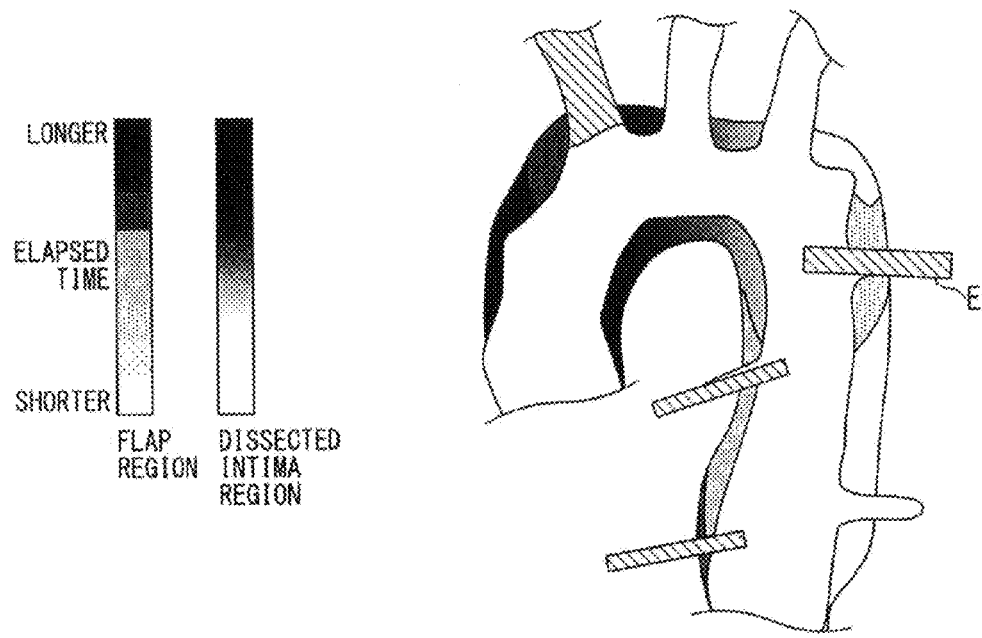
FIG. 14 is a diagram showing a first example of a second synthesized image in the ultrasonic diagnostic apparatus according to the second embodiment.

FIG. 14 is a diagram showing a first example of the second synthesized image in the ultrasonic diagnostic apparatus 1A according to the second embodiment.

FIG. 14 is a diagram showing a second synthesized image in a case where an aortic dissection has occurred and a flap region is present. The elapsed time of (at least one of) the dissected intima region and the flap region that are included in the imaging region of a previous instance of transesophageal echocardiography is calculated, and in the second synthesized image shown in FIG. 14, information on the elapsed time is synthesized onto the first synthesized image. In the second synthesized image shown in FIG. 14, gradations in each of the dissected intima region and the flap region change in accordance with the elapsed time. Note that gradations of the affecting bifurcated artery E may change in accordance with the elapsed time.

Figure 15:
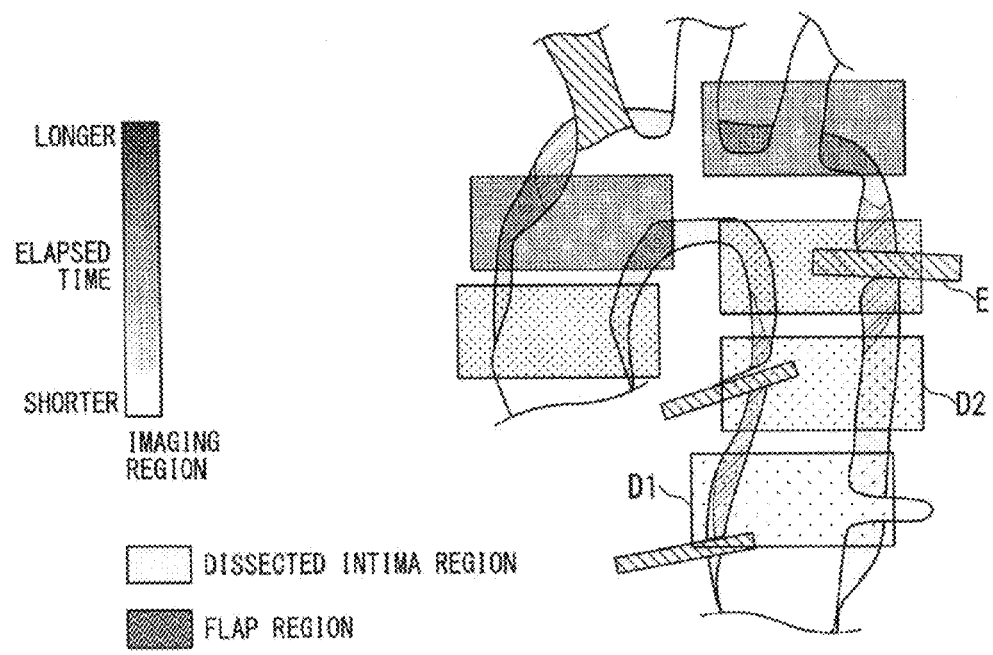
FIG. 15 is a diagram showing a second example of a second synthesized image in the ultrasonic diagnostic apparatus according to the second embodiment.

FIG. 15 is a diagram showing a second example of the second synthesized image in the ultrasonic diagnostic apparatus 1A according to the second embodiment.

FIG. 15 is a diagram showing a second synthesized image in a case where an aortic dissection has occurred and a flap region is present. The elapsed time of imaging regions D1, D2, ... of a previous instance of transesophageal echocardiography is calculated, and in the second synthesized image shown in FIG. 15, information on the imaging regions D1, D2, ... of the previous instance of transesophageal echocardiography and information on the imaging region and the elapsed time of the previous instance of transesophageal echocardiography are synthesized onto the first synthesized image. In the second synthesized image shown in FIG. 15, gradations of each of the imaging regions D1, D2, ... in transesophageal echocardiography change in accordance with the elapsed time.

Referring back to FIG. 13, the second synthesized image generating unit 73A has a function of synthesizing information on the artery region and the flap region within the imaging region in a current instance of transesophageal echocardiography that has been processed for alignment by the alignment processing unit 72 on the first synthesized image onto the current instance of a transesophageal echocardiographic image that has been generated by the image generating unit 42 to generate a third synthesized image (third synthesized image data).

Figure 16:
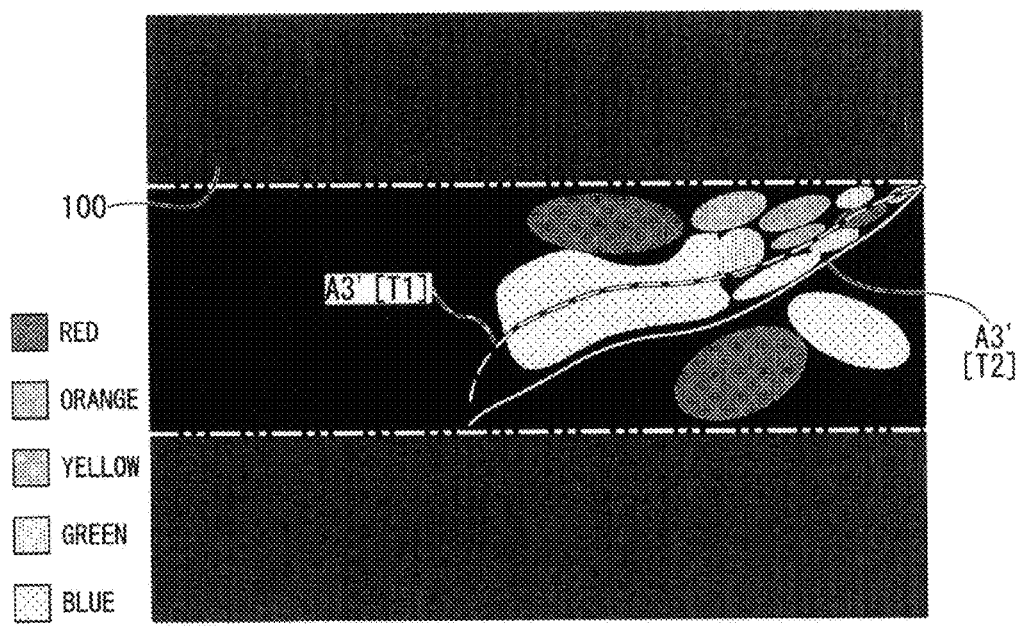
FIG. 16 is a diagram showing an example of a third synthesized image in the ultrasonic diagnostic apparatus according to the second embodiment.

FIG. 16 is a diagram showing an example of the third synthesized image in the ultrasonic diagnostic apparatus 1A according to the second embodiment.

FIG. 16 is a diagram showing a third synthesized image in a case where an aortic dissection has occurred and a flap region is present. As shown in FIG. 16, an artery region 100 within the imaging region in a current instance of transesophageal echocardiography and information on the flap regions A3'[T1] and A3'[T2] at the plurality of time phases shown in FIG. 6 are graphically synthesized onto the current instance of the transesophageal echocardiographic image. In the third synthesized image, blood is indicated in red in a region approaching the ultrasonic probe 2 and is indicated in blue in a region being distanced away from the ultrasonic probe 2. However, as the flap regions A3'[T1] and A3'[T2] appear, a turbulent flow is generated in blood within an artery, and regions of the turbulent flow are indicated in orange, yellow, green, and so forth.

According to the ultrasonic diagnostic apparatus 1A of the second embodiment, whether or not a flap has appeared in an artery within the imaging region in transesophageal echocardiography and whether or not a bifurcated artery that is affected by a flap is present can be visually recognized during an operation for an aortic dissection using transesophageal echocardiography. That is, a bifurcated artery that may be blocked by a flap can be prevented from being overlooked. Accordingly, according to the ultrasonic diagnostic apparatus 1A of the second embodiment, a flap can be confirmed with high precision during an operation for an aortic dissection using transesophageal echocardiography.

Furthermore, according to the ultrasonic diagnostic apparatus 1A of the second embodiment, whether or not a bifurcated artery that is affected is present in the dissected intima region can be visually recognized during an operation for an aortic dissection using echocardiography. That is, a risk where circulatory disturbance at an unexpected location caused by a flap moving within a range of the dissected intima is overlooked is eliminated. Accordingly, according to the ultrasonic diagnostic apparatus 1A of the second embodiment, a flap can be confirmed with high precision during an operation for an aortic dissection using echocardiography.

In addition, according to the ultrasonic diagnostic apparatus 1A of the second embodiment, the elapsed time since the final ultrasonic imaging time can be visually recognized during an operation for an aortic dissection using echocardiography. As the elapsed time can be visually recognized, it is possible to grasp which portion has been confirmed and when. In an aortic dissection, since a blood circulation condition in a blood vessel is regularly confirmed during an operation, grasping which portion has been confirmed and when makes it possible to prevent blood circulation disturbance due to a lack of confirmation. Accordingly, according to the ultrasonic diagnostic apparatus 1A of the second embodiment, a flap can be confirmed with high precision during an operation for an aortic dissection using echocardiography.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. An ultrasonic diagnostic apparatus, comprising:
   an ultrasonic probe;
   a position sensor attached to the ultrasonic probe, and configured to generate a positional data signal pertaining to a spatial coordinate position of the ultrasonic probe and a scanning direction/orientation; and
   processing circuitry configured to
      control the ultrasonic probe to execute echocardiography and to generate an echocardiographic image including an aorta and a bifurcated artery bifurcating from the aorta,
      acquire a heart area image from a storage prospectively storing the heart area image,
      extract an artery region based on the heart area image,
      identify a flap region based on the artery region,
      synthesize information on the flap region by using the artery region to generate a first synthesized image, the flap region being a region of a flap caused by intimal dissection, and the information indicating the flap region,
      perform processing to align an imaging region in the echocardiography on the heart area image based on the positional data signal, and
      synthesize additional information indicating the imaging region processed for alignment onto the first synthesized image to generate and display a second synthesized image.

2. The ultrasonic diagnostic apparatus according to claim 1,
   wherein the processing circuitry is configured to identify a dissected intima region of an aorta based on the extracted artery region and to identify the flap region from the dissected intima region based on a difference image in the heart area images that are acquired at a plurality of time phases.

3. The ultrasonic diagnostic apparatus according to claim 2, wherein
the processing circuitry is further configured to
identify a bifurcated artery that is present within a predetermined distance from the dissected intima region as an affecting bifurcated artery, and
synthesize information on the flap region and information on the affecting bifurcated artery onto the artery region to generate the first synthesized image.

4. The ultrasonic diagnostic apparatus according to claim 2,
wherein the processing circuitry is configured to identify the flap region based on a difference image in the acquired images of an end-diastolic heart area image and an end-systolic heart area image.

5. The ultrasonic diagnostic apparatus according to claim 1, wherein
the processing circuitry is further configured to
identify a bifurcated artery that is present within a predetermined distance from the flap region as an affecting bifurcated artery, and
synthesize information on the flap region and information on the affecting bifurcated artery onto the artery region to generate the first synthesized image.

6. The ultrasonic diagnostic apparatus according to claim 1,
processing circuitry is configured to synthesize information on an artery region and a flap region within the imaging region processed for alignment onto the echocardiographic image to generate a third synthesized image.

7. The ultrasonic diagnostic apparatus according to claim 1,
wherein the processing circuitry is configured to control the ultrasonic probe to execute transesophageal echocardiography and to generate a transesophageal echocardiographic image as the echocardiographic image.

8. The ultrasonic diagnostic apparatus according to claim 1, wherein the second synthesized image indicates presence or absence of the flap region in the aorta within the imaging region in the echocardiography.

9. An ultrasonic diagnosis assisting method, comprising:
controlling an ultrasonic probe to execute echocardiography and generating an echocardiographic image including an aorta and a bifurcated artery bifurcating from the aorta;
acquiring a heart area image from a storage prospectively storing the heart area image;
extracting an artery region based on the heart area image;
identifying a flap region based on the artery region;
synthesizing information on the flap region by using the artery region to generate a first synthesized image, the flap region being a region of a flap caused by intimal dissection, and the information indicating the flap region;
performing processing to align an imaging region in the echocardiography on the heart area image based on a positional data signal pertaining to a spatial coordinate position of the ultrasonic probe and a scanning direction/orientation;
synthesizing additional information indicating the imaging region processed for alignment onto the first synthesized image to generate a second synthesized image; and
displaying the second synthesized image on a display.

\* \* \* \* \*